United States Patent
Burlone et al.

(10) Patent No.: US 8,211,275 B2
(45) Date of Patent: Jul. 3, 2012

(54) METHOD OF MINIMIZING ALDEHYDE-BASED IMPURITIES IN A PROCESS STREAM

(75) Inventors: Dominick A. Burlone, Lake Jackson, TX (US); R. Merritt Sink, Lake Jackson, TX (US); Joann Lanza, Farmington Hills, MI (US); Karl Gust, Clawson, MI (US)

(73) Assignee: BASF SE, Ludwigshafen (DE)

( * ) Notice: Subject to any disclaimer, the term of this patent is extended or adjusted under 35 U.S.C. 154(b) by 1051 days.

(21) Appl. No.: 11/816,431

(22) PCT Filed: Feb. 15, 2006

(86) PCT No.: PCT/EP2006/050967
§ 371 (c)(1), (2), (4) Date: Jun. 17, 2008

(87) PCT Pub. No.: WO2006/087347
PCT Pub. Date: Aug. 24, 2006

(65) Prior Publication Data
US 2009/0114522 A1    May 7, 2009

(51) Int. Cl.
*B01D 3/34*    (2006.01)
*C07C 45/00*    (2006.01)

(52) U.S. Cl. ............................. 203/38; 203/59; 568/366

(58) Field of Classification Search .................. 203/30, 203/38, 59, 34; 568/303, 304, 338, 366
See application file for complete search history.

(56) References Cited

U.S. PATENT DOCUMENTS

| | | | | |
|---|---|---|---|---|
| 2,204,956 A | * | 6/1940 | Bresler et al. | 203/29 |
| 2,826,537 A | * | 3/1958 | Sharp et al. | 203/30 |
| 3,725,480 A | * | 4/1973 | Traise et al. | 564/367 |
| 3,898,287 A | * | 8/1975 | Gloyer | 568/410 |
| 5,399,776 A | * | 3/1995 | Fraini et al. | 568/411 |
| 6,444,096 B1 | * | 9/2002 | Barnicki et al. | 203/43 |

FOREIGN PATENT DOCUMENTS

| | | | |
|---|---|---|---|
| EP | 1433774 A1 | * | 6/2004 |
| GB | 2028329 A | * | 3/1980 |

OTHER PUBLICATIONS

Morrison, R., Boyd, R., Organic Chemistry 3rd Ed Jun. 1977. "Reactions Involving Carbanions", section 21.2 pp. 703-704, Allyn and Bacon Inc., (c) 1973.*

* cited by examiner

*Primary Examiner* — Duane Smith
*Assistant Examiner* — Patrick McCarty
(74) *Attorney, Agent, or Firm* — Connolly Bove Lodge & Hutz LLP

(57) ABSTRACT

Oxidation of an alkane to an alkanone in a process stream forms aldehyde-based impurities. A method of minimizing the aldehyde-based impurities introduces an amine into the process stream to minimize the aldehyde-based impurities. The amine interacts with the alkanone and the aldehyde-based impurities thereby forming heavy products. The method separates the heavy products from the alkanones to reduce a level of the aldehyde-based impurities. The process stream preferably includes cyclohexyl ketone as the alkanone and n-hexanal as the aldehyde-based impurity. The method is typically involved in synthesis of a caprolactam.

32 Claims, 8 Drawing Sheets

METHOD OF MINIMIZING ALDEHYDE-BASED IMPURITIES IN A PROCESS STREAM

CROSS REFERENCE TO RELATED APPLICATIONS

This application is a National Phase of International Application No. PCT/EP2006/050967 filed on Feb. 15, 2006, which claims priority to application Ser. No. 11/062,128 filed in the U.S. on Feb. 18, 2005, now abandoned, under 35 U.S.C. §120; the entire contents of all are hereby incorporated by reference.

FIELD OF THE INVENTION

The subject invention generally relates to a method of minimizing aldehyde-based impurities in a process stream. More specifically, the subject invention relates to introducing an amine into the process stream to minimize the aldehyde-based impurities.

DESCRIPTION OF THE RELATED ART

Process streams allow a constant flow of reagents to react together to form desired compounds. Typically, the process streams are used in commercial processes to synthesize the desired compounds on a large scale. For example, oxidation of alkanes to alkanones, or cyclic alkanes to cyclic alkanones, in the commercial processes is completed using the process streams. As the alkanes are oxidized to form the alkanones, many other compounds are also formed including aldehyde-based impurities. It may be desirable to separate the aldehyde-based impurities from the alkanones, i.e., from the desired compounds. This is especially important in the commercial processes that are dependent on pure alkanones with little or no impurities.

One such commercial process that is dependent on pure alkanones with little or no impurities includes synthesis of a caprolactam. The synthesis of 2-azacycloheptanone, a type of caprolactam, includes an oxidation of the cyclic alkane, cyclohexane, to the cyclic alkanone, cyclohexyl ketone, in the process stream. The synthesis also includes forming hydroxylamine in the presence of a platinum catalyst. The synthesis further includes reacting the cyclohexyl ketone with the hydroxylamine to form an oxime. The method still further provides chemically rearranging the oxime to form the caprolactam. To efficiently complete the synthesis of the caprolactam, the aldehyde-based impurities must be separated from the alkanone. If the aldehyde-based impurities are not separated, the synthesis will not proceed with high yield. Methods of separating the aldehyde-based impurities from the alkanones, such as those methods used in synthesis of the caprolactam, are known in the art.

A first prior art method of separating the aldehyde-based impurities from the alkanones only utilizes temperature differences to distill and separate the aldehyde-based impurities from the alkanones. This first prior art method is deficient because simply distilling and separating the aldehyde-based impurities from the alkanones does not remove all of the aldehyde-based impurities. Due to difficulties in removing all of the aldehyde-based impurities in practice, a range of between 600 and 900 parts of the aldehyde-based impurities per 1 million parts of the alkanone remaining after distillation is not uncommon. Therefore, the first prior art method cannot be used in the commercial processes, such as synthesis of the caprolactam, that are dependent on pure alkanones with little or no impurities.

A second prior art method utilizes a basic hydroxide or carbonate to react with the aldehyde-based impurities and form β-hydroxyaldehydes. The second prior art method separates the β-hydroxyaldehydes from the alkanones through distillation. This second prior art method is deficient because use of the basic hydroxide or carbonate promotes a self-condensation of the alkanones to produce polymeric alkanones. For descriptive purposes only, a chemical reaction schematic of the self-condensation of a representative alkanone, a cyclic alkanone, is illustrated below.

Polymerization of the alkanones renders the alkanones unusable for further processing in many commercial processes, such as synthesis of the caprolactam. Also, because the second prior art method results in up to a 25% loss of the alkanones to self-condensation, production costs are increased. Further, commercially available alkanes, the starting materials of the alkanones, and specifically cyclic alkanes, are particularly expensive. Therefore, this second prior art method is not efficient for use in the commercial processes due to increased production costs.

A prior art method of minimizing aldehyde-based impurities in a process stream, representative of the second prior art method generally described above, is disclosed in G.B. Patent App. No. 2,028,329. The '329 application discloses reacting the basic hydroxyide or carbonate, such as sodium hydroxide or sodium carbonate, with the aldehyde-based impurities present in a process stream including cyclic alkanones. The basic hydroxide or carbonate reacts with the aldehyde-based impurities to form the β-hydroxyaldehydes that can be separated by distillation. Yet, addition of the basic hydroxide or carbonate to the process stream promotes the self-condensation of the cyclic alkanones to produce the polymeric cyclic alkanones. As described above, polymerizing the alkanones renders the alkanones unusable for further processing in many commercial processes, such as synthesis of the caprolactam. The '329 application does not disclose use of amines to minimize the aldehyde-based impurities in a process stream or any method that would not promote the self-condensation of the alkanones. Therefore, the method disclosed in the '329 application is not suitable for use in the commercial processes, such as the synthesis of caprolactam, that are dependent on pure alkanones with little or no impurities.

Another prior art method of minimizing aldehyde-based impurities in a process stream, also representative of the second prior art method, is disclosed in Jap. Pat. Pub. No. JP 49-011848. The '848 publication discloses adding ammonium hydroxide to a solution of n-hexanal and cyclopentanone. The ammonium hydroxide reacts with the n-hexanal to form the β-hydroxyaldehyde. The '848 publication does not disclose the use of amines to minimize aldehyde-based impurities in the process stream. Specifically, the ammonium hydroxide is a basic hydroxide and is not an amine. Therefore, the ammonium hydroxide promotes the self-condensation of the cyclic alkanones, as described above. Therefore, the method disclosed in the '848 publication is not suitable for use in the commercial processes, such as synthesis of the caprolactam, that are dependent on pure, monomeric cyclic alkanones with little or no impurities.

The various prior art methods described above are not suitable for use in the commercial processes, such as synthesis of the caprolactam, for a variety of reasons. These prior art methods have not been optimized for use in the commercial processes to reduce the production costs. The basic hydroxide or carbonate such as ammonium hydroxide, sodium hydroxide, or sodium carbonate, when added to the alkanones, promote the self-condensation of the alkanones. Any self-condensation of the alkanones reduces useable products and increases the production costs. Also, distilling and separating the aldehyde-based impurities from the alkanones does not easily eliminate all of the aldehyde-based impurities in practice. Therefore, neither of the prior art methods can be used in cost efficient commercial processes that are dependent on pure alkanones with little or no impurities.

SUMMARY OF THE INVENTION AND ADVANTAGES

The subject invention provides a method of minimizing aldehyde-based impurities in a process stream. The process stream includes an alkanone and the aldehyde-based impurities. The method includes the step of introducing an amine into the process stream to form a heavy product. The method also includes the step of separating the alkanone from the heavy product.

The method of minimizing the aldehyde-based impurities in the process stream, according to the subject invention, is used to decrease industrial production costs. The method utilizes the amines to form heavy products that are separated from the alkanones. By forming heavy products, the amines significantly reduce levels of the aldehyde-based impurities in the process stream. The amines also minimize self-condensation of the alkanones which, ultimately, decreases overall production costs.

DETAILED DESCRIPTION OF A PREFERRED EMBODIMENT

A method of minimizing aldehyde-based impurities in a process stream is provided. The process stream of the subject invention includes an alkanone and the aldehyde-based impurities. The alkanone in the process stream is a desired product of an oxidation of an alkane. The oxidation of the alkane produces the alkanone, an alcohol, and the aldehyde-based impurities, in addition to non-aldehyde based impurities such as peroxides, ethers, and diols.

Preferably, the process stream includes a cyclic alkanone as a desired product of an oxidation of a cyclic alkane. If the method of the subject invention includes the cyclic alkanone, the cyclic alkanone can be used in synthesis of a caprolactam, which can be polymerized to form a nylon final product. Any aldehyde-based impurities present with the cyclic alkanone in the process stream can contaminate the synthesis of the caprolactam and reduce commercial viability of the caprolactam. Therefore, the aldehyde-based impurities are preferably minimized.

Synthesis of the caprolactam includes reacting the cyclic alkanone with an amine to form an oxime. The oxime chemically rearranges to form the caprolactam. One example of the caprolactam includes 2-azacycloheptanone. The caprolactam can be polymerized to form the nylon final product which is commercially sold. A sample chemical synthetic scheme for synthesis of the caprolactam is illustrated below.

[Beckman Rearrangement]

2-azacycloheptanone
(Caprolactam)

To efficiently complete synthesis of the caprolactam, the aldehyde-based impurities must be separated from the cyclic alkanone. If the aldehyde-based impurities are not separated, the synthesis will not proceed with high yield.

The cyclic alkanone that is used to form the caprolactam is preferably present in the process stream. If included in the process stream, the cyclic alkanone preferably includes, but is not limited to, cyclohexyl ketone. However, the cyclic alkanone may also include cyclopentanones, cycloheptanones, cyclooctanones, and combinations thereof. The cyclohexyl ketone can be either substituted or unsubstituted. If unsubstituted, the cyclohexyl ketone is commonly referred to as cyclohexanone. For descriptive purposes only, a chemical structure of unsubstituted cyclohexyl ketone (i.e., cyclohexanone) is illustrated below.

In addition to the alkanone present in the process stream, the alcohol may also be pre-sent in the process stream, originating from the oxidation of the alkane. The alcohol that may be present in the process stream preferably includes, but is not limited to, a cyclic alcohol. Most preferably, the alcohol, if present, includes cyclohexyl alcohol. For descriptive purposes only, a chemical structure of cyclohexyl alcohol is illustrated below.

The aldehyde-based impurities that reduce the commercial viability of the caprolactam and that are present in the process stream include, but are not limited to, a hexanal. Typically, the aldehyde-based impurities include n-hexanal. For descriptive purposes only, a chemical structure of n-hexanal is illustrated below.

The method of minimizing aldehyde-based impurities in the process stream generally includes the steps of introducing the amine into the process stream to form a heavy product and separating the alkanone from the heavy product. The step of separating the alkanone from the heavy product is discussed below in greater detail.

Preferably, the amine introduced into the process stream includes monomeric amines, polymeric amines, and combinations thereof. The terminology "polymeric amine" includes any molecule including $[-RN-(CR_2)_m-NR-]_n$, wherein R includes a hydrogen or a hydrocarbon group including any straight chain, branched, or cyclic hydrocarbon, m includes any integer preferably of from 1 to 10, more preferably of from 2 to 6, and most preferably of from 2 to 3, and n includes any integer preferably of from 1 to 10, more preferably of from 2 to 6, and most preferably of from 2 to 3. It is contemplated that the terminology "polymeric amine" also includes a molecule having any type of polymeric backbone having amine functionality on the polymeric backbone. Most preferably the amine includes ethylenediamine, diethylenetriamine (DETA), triethylenetetramine (TETA), and combinations thereof. That is, only one amine is necessary to introduce into the process stream, but a combination may be introduced into the process stream. For descriptive purposes only, chemical structures of ethylenediamine, DETA, and TETA, are shown below, respectively.

The amine is preferably introduced into the process stream in an amount of from 0.1 to 10, and most preferably of from 0.5 to 3 molar equivalents of the amine compared to the aldehyde-based impurities.

The amine can be introduced into the process stream at various points. Preferably, the amine is introduced into a process vessel or a process line, such as a distillation tower, after the alkanone and the aldehyde-based impurities are formed from the oxidation of the alkane. As such, the distillation tower includes the alkanone and the aldehyde-based impurities when the amine is introduced.

Introducing the amine into the process stream may include the step of interacting the amine with the aldehyde-based impurities to form the heavy product. The heavy product formed from interacting the amine with the aldehyde-based impurities includes an imine. The imine has a higher boiling point than either the alkanone or the aldehyde-based impurities. Therefore, if desired, the higher boiling point of the imine can be exploited for distillation purposes.

The step of interacting the amine may also include the step of chemically reacting the alkanone with the aldehyde-based impurities to form an alkylenyl alkanone as the heavy product. Without intending to be limited by any particular theory, it is believed that the amine may facilitate forming the alkylenyl alkanone. Preferably, if the cyclic alkanone is included in the process stream, the cyclic alkanone will chemically react with the aldehyde-based impurities to form an alkylenyl cyclic alkanone.

The terminology "alkylenyl cyclic alkanone" refers to a chemical compound that includes a cyclic alkanone moiety represented as $O=C_mR_n-$ and an alkylenyl moiety represented as $-C_kR_p$. Referring to the cyclic alkanone moiety, $O=C_mR_n-$ includes a cyclic molecule wherein m includes any integer of from 3 to 10, n includes any integer of from (2m minus 4) to (2m minus 3), and R includes a hydrogen group, an alkyl or alkenyl group having up to 6 carbon atoms, and combinations thereof. Referring now to the alkylenyl moiety, $-C_kR_p$ includes a linear alkylenyl molecule wherein k includes any integer of from 2 to 10, p includes any integer of from (2k minus 1) to (2k), and R includes a hydrogen group, an alkyl or alkenyl group having up to 6 carbon atoms, and combinations thereof.

Typically, if formed, the alkylenyl cyclic alkanone includes, but is not limited to, an alkylenyl cyclic hexanone. Without intending to be limited by any particular theory, it is believed that if the cyclohexyl ketone is reacted with the n-hexanal, a specific alkylenyl cyclic hexanone, 2-hexylidene-cyclohexanone, will be formed. Representative chemical formulas of 2-hexylidene-cyclohexanone include $O=C_6H_8=C_6H_{12}$ and $O=C_6H_9-C_6H_{11}$ depending on where a double bond resides.

For descriptive purposes only, a chemical structure of 2-hexylidene-cyclohexanone is illustrated below.

Like the imine, the alkylenyl alkanone also has a higher boiling point than either the alkanone or the aldehyde-based impurities. As such, the higher boiling point of the alkylenyl alkanone may also be exploited for distillation purposes.

The amine may be introduced into the process stream by injection. If the amine is injected into the process stream, it is preferred that the amine is injected into the distillation tower, as introduced above.

Referring now to the step of separating the alkanone from the heavy product, i.e., the imine and/or the alkylenyl alkanone, the step may include the step of distilling the heavy product and the alkanone. If the heavy product and the alkanone are distilled, it is preferred that the step of distilling the heavy product and the alkanone includes the step of distilling at a temperature of from 150° C. to 170° C. and more preferably of from 155° C. to 165° C.

In commercial applications, it is most preferred that the process stream undergoes a series of distillations in multiple distillation towers to adequately separate the alkanone from the heavy product. If the process stream undergoes the series of distillations, a first distillation in a first distillation tower, without the amine, may remove a portion of the aldehyde-based impurities as a tops product. The terminology "tops product" refers to a compound removed from a top of the distillation tower. While a portion of the aldehyde-based impurities may be removed as the tops product, the alkanone may remain in a bottom of the first distillation tower and be removed as a bottoms product. The terminology "bottoms product" refers to a compound removed from the bottom of the distillation tower. In the first distillation, the process stream is preferably distilled at a temperature of from 120° C. to 140° C. and more preferably of from 128° C. to 132° C. To aid in minimizing the n-hexanal in the process stream in the bottom of the first distillation tower, the amine may be introduced into the bottom of the first distillation tower. As explained above, if the amine is introduced into the first distillation tower, the amine may chemically react with the alkanone to form the imine, and the alkanone may chemically react with the aldehyde-based impurities to form the alkylenyl alkanone as the heavy products, respectively. If the amine is introduced into the bottom of the first distillation tower, the process stream including the alkanone, any remaining aldehyde-based impurities, and the heavy products preferably flows as the bottoms product into a second distillation tower for a second distillation.

If the second distillation occurs in the second distillation tower, the process stream, at this point, preferably includes only the alkanone and the heavy products. It is to be understood that remaining aldehyde-based impurities may be unavoidably present in the process stream due to incomplete removal as the tops product in the first distillation or incomplete chemical reaction with the alkanone. Preferably, pure alkanone is removed as the tops product from a top of the second distillation tower and the process stream flows as the bottoms product into a bottom of the third distillation tower. In the second distillation tower, the process stream is preferably distilled at a temperature of from 150° C. to 170° C. and more preferably of from 155° C. to 165° C.

If the process stream flows into the third distillation tower, the process stream preferably includes only the heavy products. It is to be understood that remaining aldehyde-based impurities and remaining alkanone may continue to be unavoidably present in the process stream with the heavy products. If the process stream is distilled in the third distillation tower, the heavy products preferably remain in the bottom of the third distillation tower. It is contemplated that the heavy products may flow as bottom products into other distillation towers for additional distillation, if necessary.

In another embodiment of the subject invention, the subject invention may include the step of adjusting a pH of the process stream at various points in the method. If the pH of the process stream is adjusted, it is preferably adjusted to from 2 to 7. More preferably, the pH is adjusted to from 3 to 5. The step of adjusting the pH of the process stream may include the step of adding an acid to the process stream. Preferably the acid includes, but is not limited to, an organic acid. Most preferably the acid includes formic acid.

Optionally, the process stream including the amine may be heated at various points in the method. Without intending to be bound by theory, it is believed that heating the process stream increases a kinetic chemical reaction of the aldehyde-based impurities and the alkanone, thus aiding in minimizing the aldehyde-based impurities. If the process stream is heated, the process stream is preferably heated to from 130° C. to 170° C. and more preferably of from 130° C. to 150° C.

The method, according to the subject invention, that minimizes aldehyde-based impurities in the process stream yields multiple advantages, including decreasing industrial production costs. The method utilizes the amine to form the heavy products. As explained above, the formation of the heavy products is beneficial because it allows for separation of the heavy products from the pure alkanone. By forming the heavy products, the amine significantly reduces levels of the aldehyde-based impurities in the process stream, which includes the alkanone. The amine also minimizes possible self-condensation of the alkanones, which would raise the industrial production costs through loss of the desired alkanone.

Figure 1:
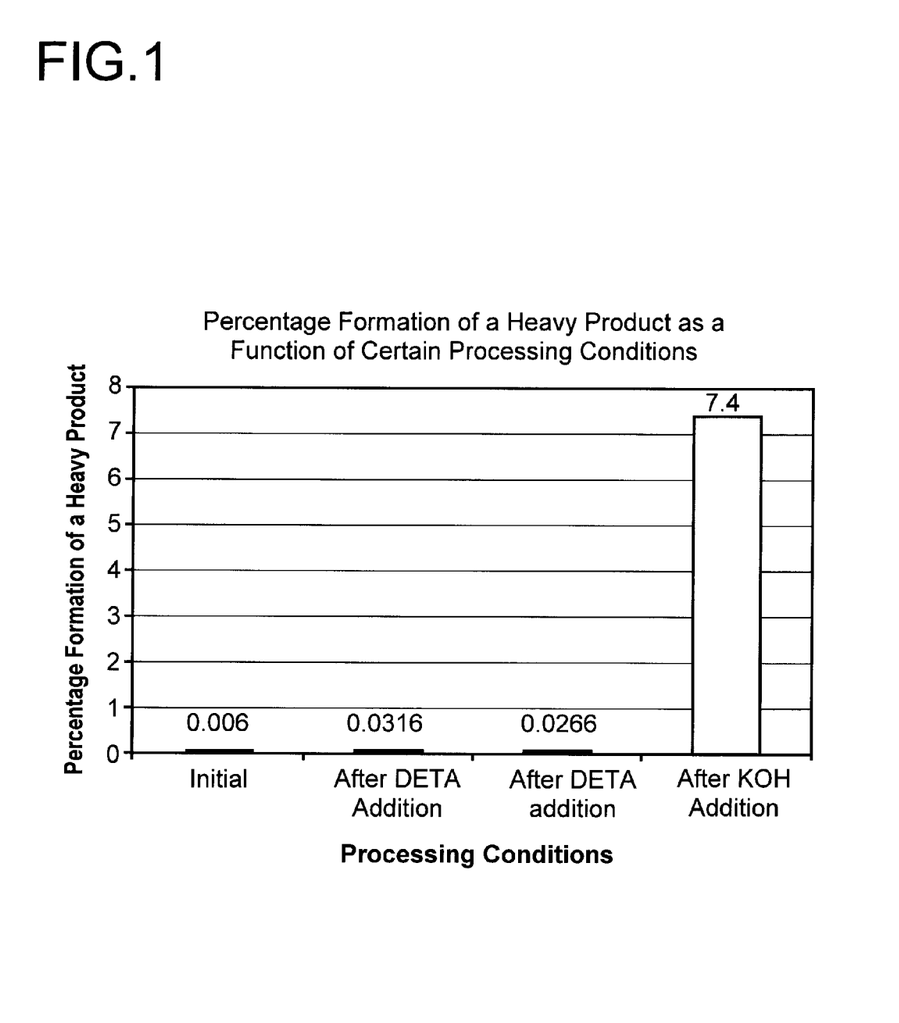
FIG. 1 is a bar graph illustrating a percentage formation of a heavy product as a function of certain processing conditions.

Referring now to FIG. 1, addition of potassium hydroxide to a 50:50 mixture of the cyclohexyl ketone and the cyclohexyl alcohol is illustrated as a control representing the prior art of the addition of the potassium hydroxide to the cyclic alkanones. The addition of the potassium hydroxide to the mixture greatly increases the formation of the heavy products including the self-condensation product of the cyclic alkanone and a β-hydroxyaldehyde, as disclosed in the prior art. FIG. 1 also illustrates that addition of the DETA and the TETA to the 50:50 mixture of the cyclohexyl ketone and the cyclohexyl alcohol including the n-hexanal greatly decreases the formation of the heavy products thereby decreasing the self-condensation product of the cyclohexyl ketone and reducing production costs.

Figure 2:
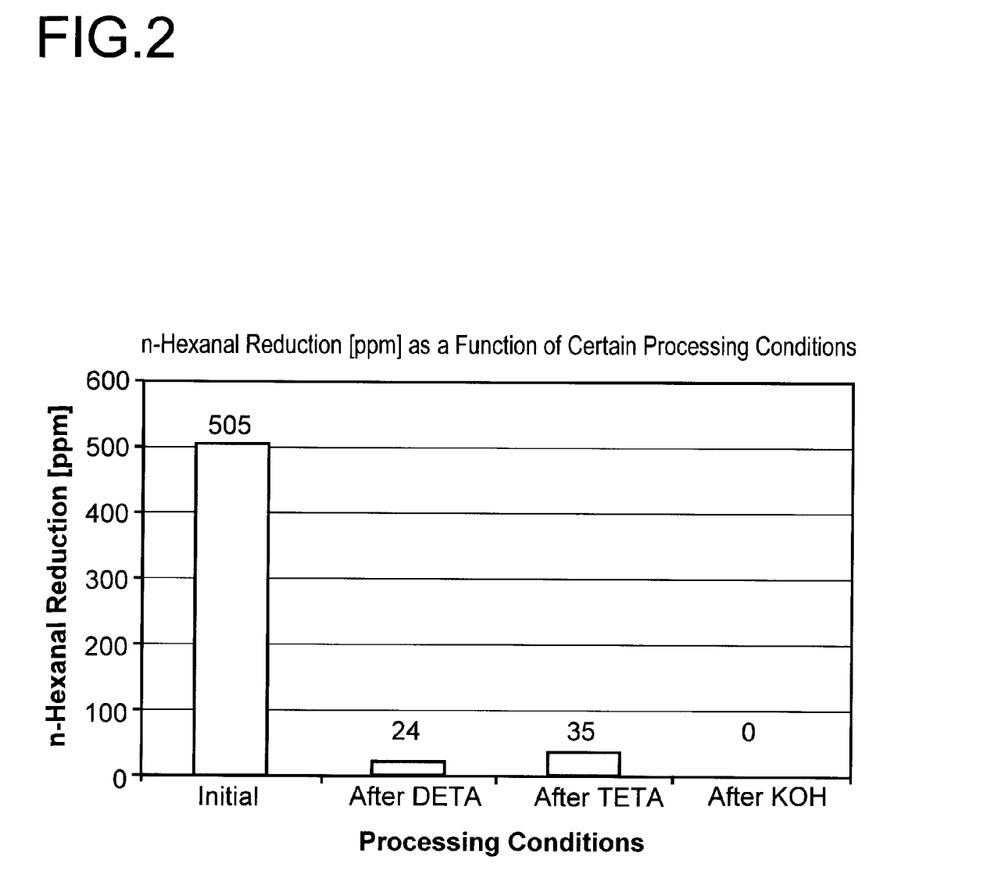
FIG. 2 is a bar graph illustrating n-hexanal reduction as a function of certain processing conditions.

Referring now to FIG. 2, addition of the potassium hydroxide to a 50:50 mixture of the cyclohexyl ketone and the cyclohexyl alcohol including the n-hexanal is illustrated as a control representing the prior art of the addition of the potassium hydroxide to the cyclic alkanones. The addition of the potassium hydroxide to the mixture totally removed the n-hexanal in the mixture. FIG. 2 also illustrates that addition of the DETA and the TETA to the mixture greatly decreased the n-hexanal concentration in the mixture. Therefore, addition of the DETA or TETA to the mixture is effective in reducing the aldehyde-based impurities in the process stream.

In both FIGS. 1 and 2, the terminology "Initial" indicates that no amine was added to the 50:50 mixtures of the cyclohexyl ketone and the cyclohexyl alcohol. The terminology "After DETA addition" indicates that 1.5 molar equivalents of the DETA to the n-hexanal was added to 50:50 mixtures of the cyclohexyl ketone and the cyclohexyl alcohol. The terminology "After TETA addition" indicates that 1.5 molar equivalents of the TETA to the n-hexanal was added to 50:50 mixtures of the cyclohexyl ketone and the cyclohexyl alcohol. The terminology "After KOH indicates" that 1.5 molar equivalents of potassium hydroxide to the n-hexanal was added to 50:50 mixtures of the cyclohexyl ketone and the cyclohexyl alcohol, as disclosed in the prior art. In all of the aforementioned conditions, the mixtures were refluxed for 10 minutes after addition of the amine to the 50:50 mixture, and gas chromatography measurements were taken after 10 minutes of reflux of the 50:50 mixtures.

Figure 3:
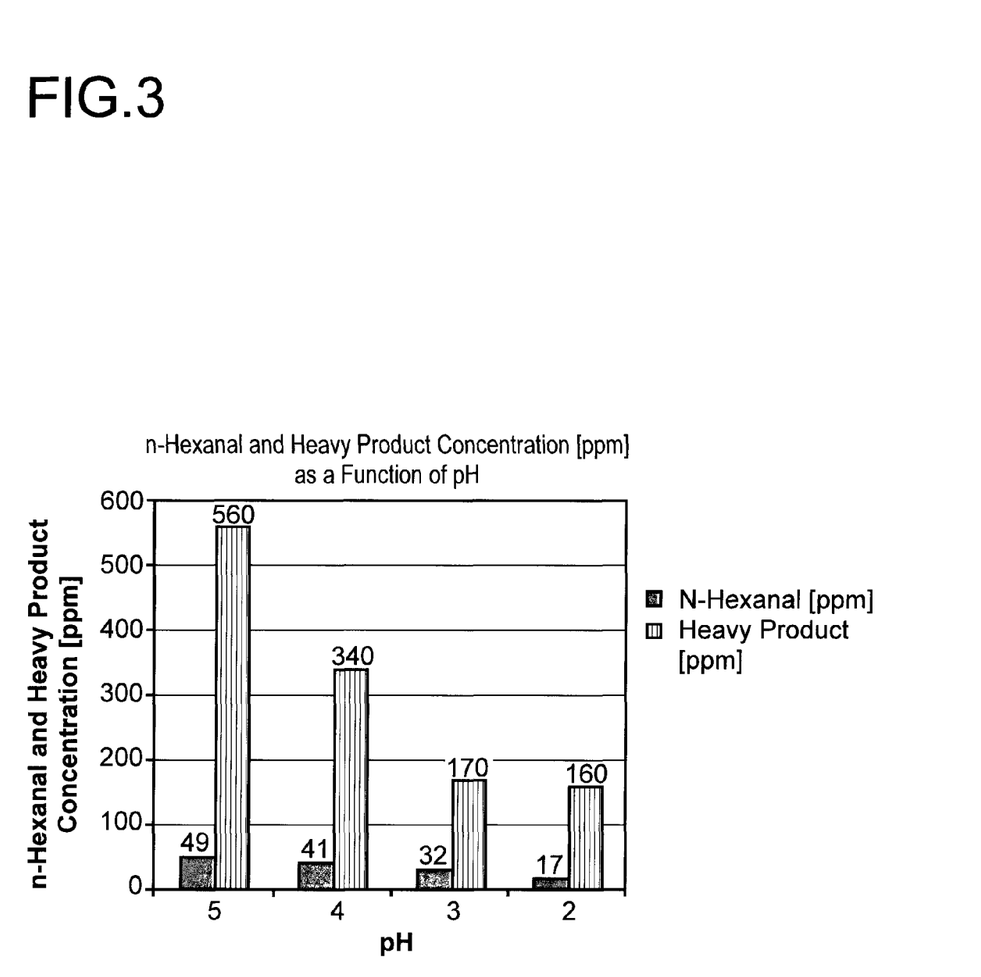
FIG. 3 is a bar graph illustrating n-hexanal and heavy product concentration as a function of pH.

Referring now to FIG. 3, addition of the formic acid to 50:50 mixtures of the cyclohexyl ketone and the cyclohexyl alcohol including the n-hexanal is illustrated. The addition of the formic acid adjusts the pH of the mixtures to 2, 3, 4, or 5. FIG. 3 also shows that a decrease in pH results in a decrease in formation of the heavy products and a decrease in the n-hexanal concentration in the mixtures. Therefore, a lower pH of the mixtures may result in decreased production costs that would result from loss of the cyclic alkanone.

In FIG. 3, the terminology "5" indicates the formic acid was added to a 50:50 mixture of the cyclohexyl ketone and the cyclohexyl alcohol to adjust the pH to 5. 1 molar equivalent of the DETA to the n-hexanal was added to the mixture. The terminology "4" indicates the formic acid was added to a 50:50 mixture of the cyclohexyl ketone and the cyclohexyl alcohol to adjust the pH to 4. 1 molar equivalent of the DETA to the n-hexanal was added to the mixture. The terminology "3" indicates the formic acid was added to a 50:50 mixture of the cyclohexyl ketone and the cyclohexyl alcohol to adjust the pH to 3. 1 molar equivalent of the DETA to the n-hexanal was added to the mixture. The terminology "2" indicates the formic acid was added to a 50:50 mixture of the cyclohexyl ketone and the cyclohexyl alcohol to adjust the pH to 2. 1 molar equivalent of the DETA to the n-hexanal was added to the mixture. In all of the aforementioned conditions, gas chromatography measurements were taken after addition of DETA to the 50:50 mixtures.

Figure 4:
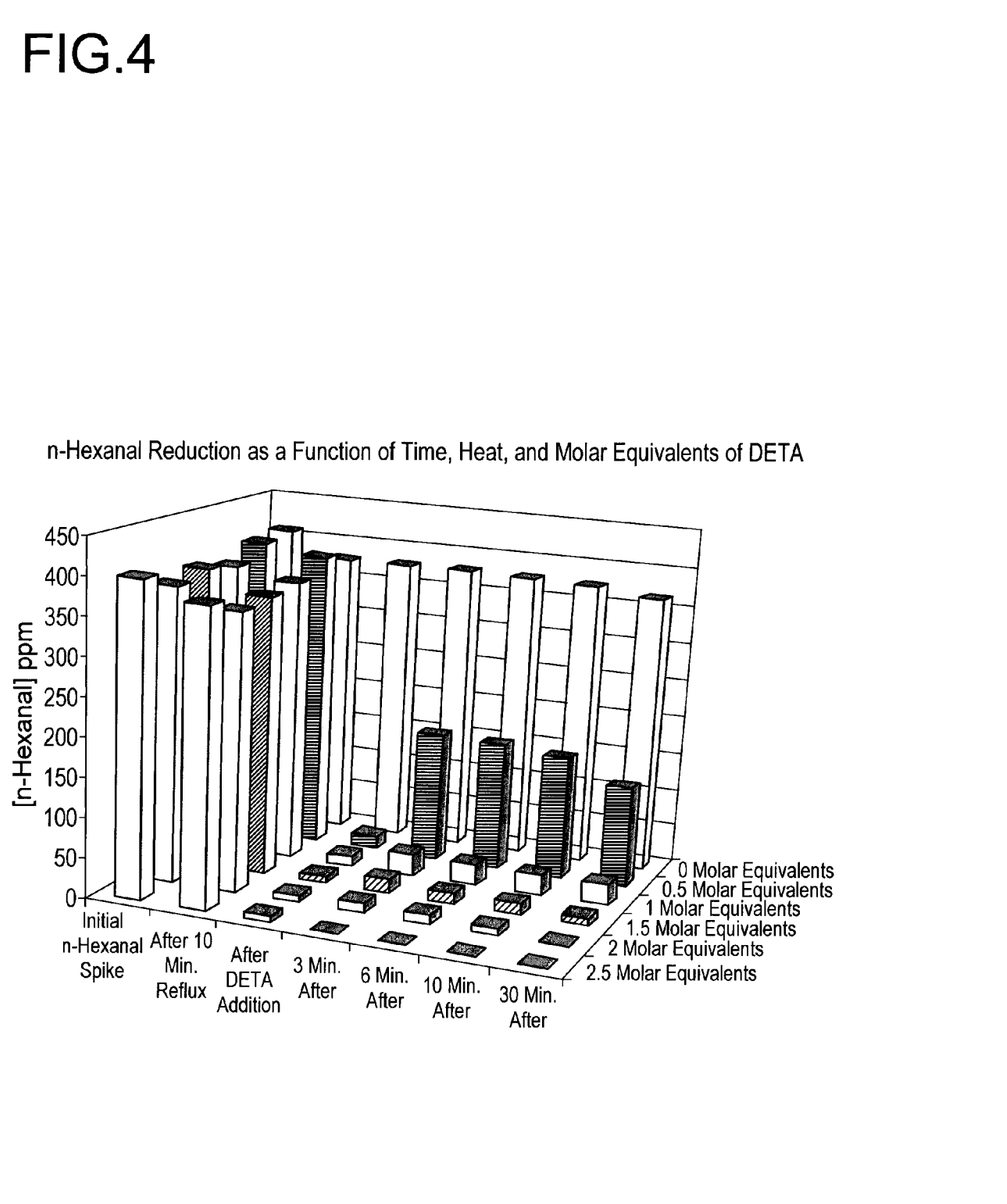
FIG. 4 is a three-dimensional bar graph illustrating n-hexanal reduction as a function of time, heat, and molar equivalents of diethylenetriamine (DETA)
Figure 5:
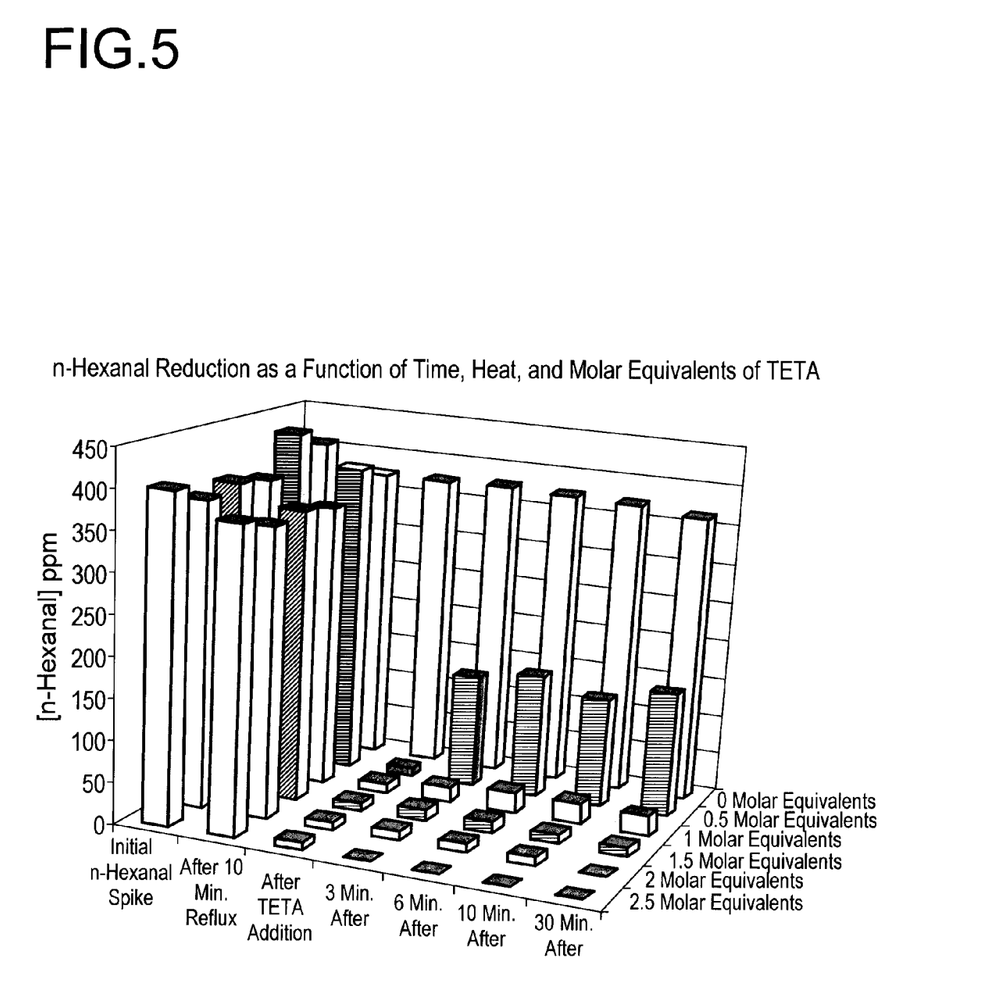
FIG. 5 is a three-dimensional bar graph illustrating n-hexanal reduction as a function of time, heat, and molar equivalents of triethylenetetramine (TETA)

Referring now to FIGS. 4 and 5, approximately 400 ppm of the n-hexanal was added to 50:50 mixtures of the cyclohexyl ketone and the cyclohexyl alcohol such that a degradation of the n-hexanal could be measured via gas chromatography measurements. The 50:50 mixtures were adjusted to a pH of 6 with addition of the formic acid. The DETA and the TETA were added to the 50:50 mixtures in FIGS. 4 and 5, respectively. The DETA and the TETA were added to the 50:50 mixtures under reflux in 0.5, 1, 1.5, 2, and 2.5 molar equivalents to the n-hexanal. Gas chromatography measurements were taken at times zero, after 10 minutes of reflux before amine addition, at times zero after the DETA or the TETA addition, and at times 3, 6, 10, and 30 minutes after the DETA or the TETA addition. FIGS. 4 and 5 also show the n-hexanal reduction as a function of time, heat, and molar equivalents of the DETA or the TETA. FIGS. 4 and 5 also show a substantial decrease in the n-hexanal concentration in the mixtures after addition of the DETA or the TETA. Therefore, upon pH adjustment, addition of the amine and addition of heat, the aldehyde-based impurities in the process stream are reduced, thus lowering production costs.

Figure 6:
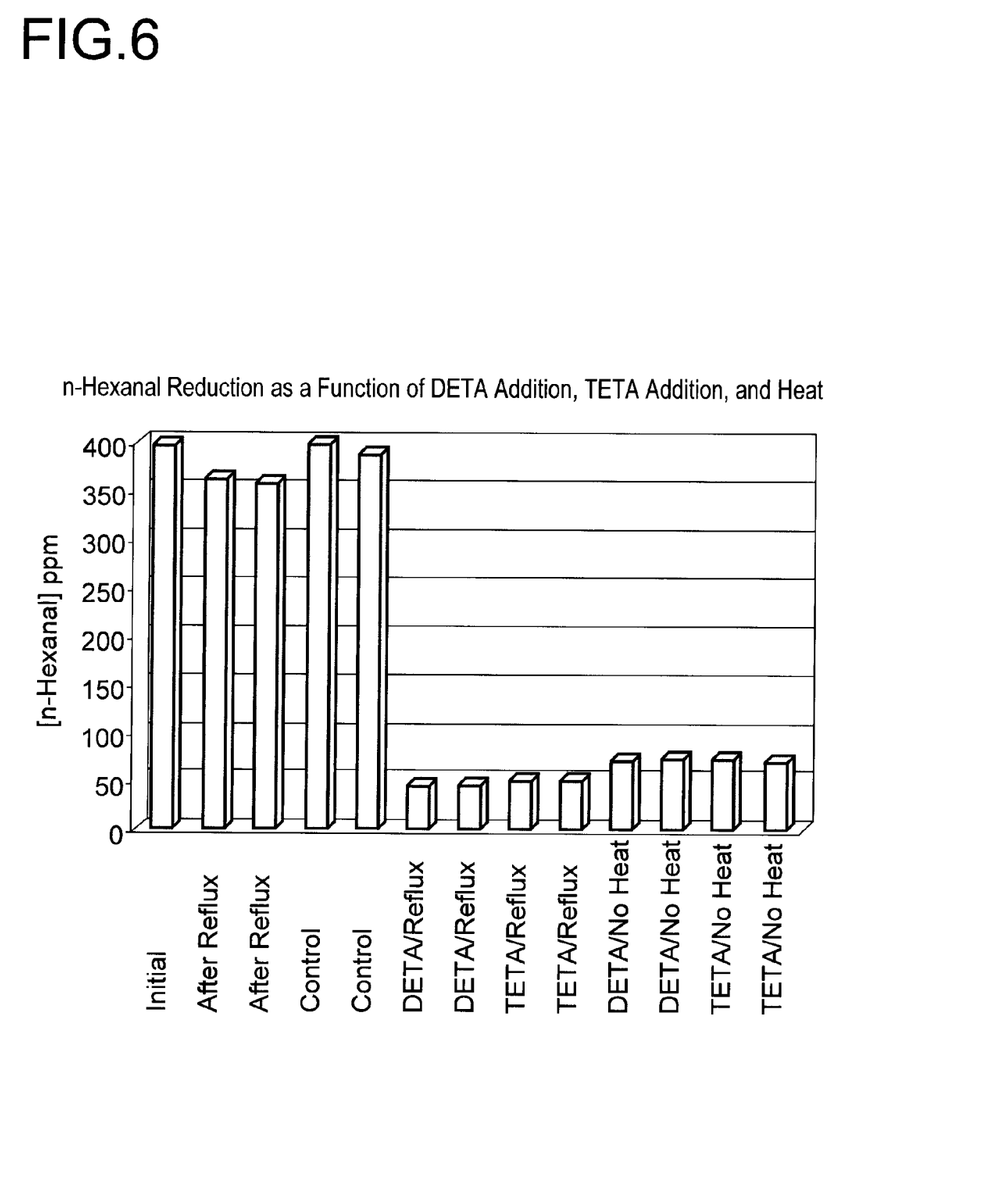
FIG. 6 is a three-dimensional bar graph illustrating n-hexanal reduction as a function of DETA addition, TETA addition, and heat.

Referring now to FIG. 6, approximately 400 ppm of the n-hexanal was added to 50:50 mixtures of the cyclohexyl ketone and the cyclohexyl alcohol such that a degradation of the n-hexanal could be measured via gas chromatography measurements. The 50:50 mixtures were adjusted to a pH of 6 with addition of the formic acid. The mixture was separated into multiple samples, the DETA or the TETA was added to the samples, and some samples were heated. FIG. 6 depicts a small reduction in the n-hexanal concentration with only addition of heat. FIG. 6 also depicts a larger reduction in the n-hexanal concentration with addition of the DETA or the TETA and optional heat. Therefore, upon pH adjustment, addition of the amine and addition of heat, the aldehyde-based impurities in the process stream are reduced, thus lowering production costs.

Figure 7:
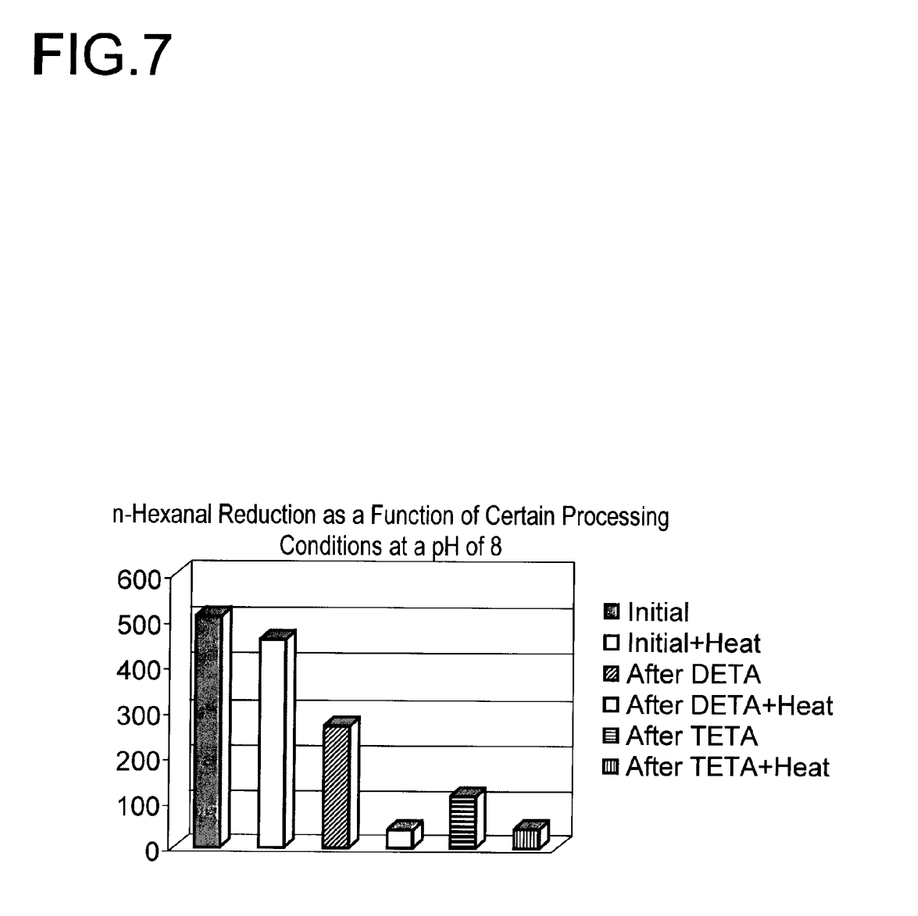
FIG. 7 is a three-dimensional bar graph illustrating n-hexanal reduction as a function of certain processing conditions at a pH of 8.

Referring now to FIG. 7, a reduction in the n-hexanal concentration with addition of the DETA or the TETA and optional heat is illustrated. Approximately 400 ppm of the n-hexanal was added to 50:50 mixtures of the cyclohexyl ketone and the cyclohexyl alcohol such that a degradation of the n-hexanal could be measured via gas chromatography measurements. The 50:50 mixtures were unadjusted to a pH of 8. The mixture was separated into multiple samples, the DETA or the TETA was added to the samples, and some of the samples were heated. FIG. 7 depicts a small reduction in the n-hexanal concentration with only addition of heat. FIG. 7 also depicts a larger reduction in the n-hexanal concentration with addition of the DETA or the TETA and optional heat. Therefore, upon addition of the amine and addition of heat, the aldehyde-based impurities in the process stream are reduced, thus lowering production costs.

Figure 8:
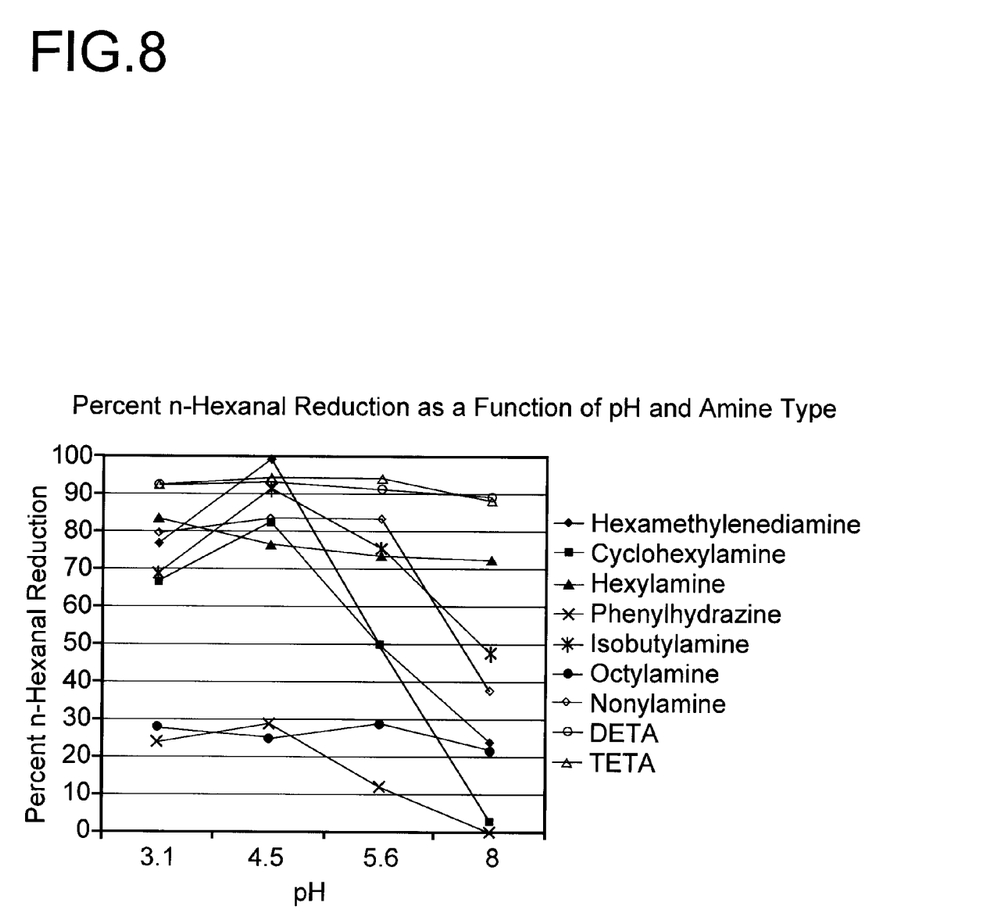
FIG. 8 is a line graph illustrating a percentage of n-hexanal reduction as a function of pH and amine type.

Referring now to FIG. 8, the DETA and the TETA effectively reduce the n-hexanal concentration in a process stream including cyclohexyl ketone and n-hexanal. The n-hexanal was added to 50:50 mixtures of the cyclohexyl ketone and the cyclohexyl alcohol such that a degradation of the n-hexanal could be measured via gas chromatography measurements. The 50:50 mixtures were adjusted to a pH of 3.1, 4.5, 5.6, and 8 with addition of the formic acid. 3 molar equivalents of different amines to the n-hexanal were added to the mixtures. Gas chromatography measurements were taken before and after 60 minutes of reflux of the mixtures. Therefore, FIG. 8 shows that DETA and TETA are the most effective amines for reducing the aldehyde-based impurities in the process stream, thus maximizing the reduction of production costs.

The following examples generally illustrate the nature of the invention and are not to be construed as limiting the invention. Unless otherwise indicated, all parts are given as parts per million.

EXAMPLES

The method of minimizing aldehyde-based impurities in the process stream including the alkanone and the aldehyde-based impurities includes introducing the amine into the process stream to form the heavy product. The amine interacts with the alkanone and the aldehyde-based impurities to form the heavy product, and it is contemplated that more than one heavy product may be formed. The heavy product is separated from the alkanone, preferably through distillation.

According to the subject invention, the amines were added to 50:50 mixtures of cyclohexyl ketone and cyclohexyl alcohol including n-hexanal. The amines interacted with the n-hexanal to form the imine. The cyclohexyl ketone interacted with the n-hexanal, in the presence of the amine, to form 2-hexylidene-cyclohexanone.

TABLE 1 n-Hexanal Reduction as a Function of DETA Added

| 4.6 Equivalents of DETA Added; pH = 4.6 | | | 8.8 equivalents of DETA Added; pH = 4.5 | | | 13.4 equivalents of DETA Added; pH = 4.5 | | |
|---|---|---|---|---|---|---|---|---|
| n-Hexanal [ppm] | Time (h) | % n-Hexanal Reduction | n-Hexanal (ppm) | Time (h) | % n-Hexanal Reduction | n-Hexanal (ppm) | Time (h) | % n-Hexanal Reduction |
| 415 | Before Addition | 0 | 415 | Before Addition | 0 | 415 | Before Addition | 0 |
| 53 | 0.1 | 87.2 | 35 | 0.1 | 91.6 | 26 | 0.1 | 93.7 |
| 50 | 0.5 | 88 | 31 | 0.5 | 92.5 | 22 | 0.5 | 94.7 |
| 49 | 12 | 88.2 | 29 | 12 | 93 | 20 | 12 | 95.2 |

Table 1 shows n-hexanal reduction in a 50:50 mixture of cyclohexyl ketone and cyclohexyl alcohol including 415 parts per million of n-hexanal at time 0. A pH of the mixture was adjusted with addition of formic acid. Table 1 also shows DETA added in three quantities to identical samples of the mixture. The samples were stirred at room temperature and gas chromatography measurements of the samples were taken at times 0, 0.1, 0.5, and 12 hours after addition of DETA.

TABLE 2 n-Hexanal Reduction as a Function of DETA Added DETA Added; pH = 8; Room Temperature; n-Hexanal [ppm]

| Time (h) | 1 Molar Equiv. | 2 Molar Equiv. | 3 Molar Equiv. | 4 Molar Equiv. | 5 Molar Equiv. |
|---|---|---|---|---|---|
| Before Addition | 324 | 324 | 324 | 324 | 324 |
| 0.1 | 123 | 105 | 94 | 88 | 84 |
| 0.5 | 114 | 100 | 89 | 84 | 80 |
| 1 | 106 | 93 | 86 | 78 | 79 |
| 12 | 86 | 78 | 77 | 72 | 70 |

Table 2 shows n-hexanal reduction in a 50:50 mixture of cyclohexyl ketone and cyclohexyl alcohol including 324 parts per million of n-hexanal at time 0. A pH of the mixture was unadjusted at 8. Table 2 also shows DETA added in five quantities to five identical samples in 1, 2, 3, 4 and 5 molar equivalents to n-hexanal. The samples were stirred at room temperature and gas chromatography measurements of the samples were taken at times 0, 0.1, 0.5, 1, and 12 hours after addition of DETA.

TABLE 3 n-Hexanal Reduction as a Function of DETA Added DETA Added; pH = 4.5; Room Temperature; n-Hexanal [ppm]

| Time (h) | 1 Molar Equiv. | 2 Molar Equiv. | 3 Molar Equiv. | 4 Molar Equiv. | 5 Molar Equiv. |
|---|---|---|---|---|---|
| Before Addition | 305 | 305 | 305 | 305 | 305 |
| 0.1 | 48 | 34 | 35 | 30 | 32 |
| 0.5 | 38 | 36 | 34 | 32 | 29 |
| 1 | 38 | 35 | 33 | 31 | 30 |
| 12 | 36 | 32 | 27 | 23 | 22 |

Table 3 shows n-hexanal reduction in a 50:50 mixture of cyclohexyl ketone and cyclohexyl alcohol including 305 parts per million of n-hexanal at time 0. A pH of the mixture was adjusted to 4.5 with addition of formic acid. Table 3 also shows DETA added in five quantities to five identical samples in one, two, three, four, and five molar equivalents to n-hexanal. The samples were stirred at room temperature and gas chromatography measurements of the samples were taken at times 0, 0.1, 0.5, 1, and 12 hours after addition of DETA.

TABLE 4 n-Hexanal Reduction as a Function of TETA Added TETA Added; pH = 8; Room Temperature; n-Hexanal [ppm]

| Time (h) | 1 Molar Equiv. | 2 Molar Equiv. | 3 Molar Equiv. | 4 Molar Equiv. | 5 Molar Equiv. |
|---|---|---|---|---|---|
| Before Addition | 324 | 324 | 324 | 324 | 324 |
| 0.1 | 198 | 142 | 125 | 102 | 94 |
| 0.5 | 174 | 127 | 108 | 95 | 88 |
| 1 | 176 | 115 | 101 | 92 | 82 |
| 12 | 194 | 131 | 96 | 83 | 87 |

Table 4 shows n-hexanal reduction in a 50:50 mixture of cyclohexyl ketone and cyclohexyl alcohol including 324 parts per million of n-hexanal at time 0. A pH of the mixture was unadjusted at 8. Table 4 also shows TETA added in five quantities to five identical samples in 1, 2, 3, 4 and 5 molar equivalents to n-hexanal. The samples were stirred at room temperature and gas chromatography measurements of the samples were taken at times 0, 0.1, 0.5, 1, and 12 hours after addition of TETA.

TABLE 5 n-Hexanal Reduction as a Function of TETA Added TETA Added;
pH = 4.5; Room Temperature; n-Hexanal [ppm]

| Time (h) | 1 Molar Equiv. | 2 Molar Equiv. | 3 Molar Equiv. | 4 Molar Equiv. | 5 Molar Equiv. |
|---|---|---|---|---|---|
| Before Addition | 318 | 318 | 318 | 318 | 318 |
| 0.1 | 47 | 38 | 31 | 32 | 27 |
| 0.5 | 31 | 35 | 30 | 30 | 25 |
| 1 | 33 | 30 | 28 | 30 | 25 |
| 12 | 45 | 34 | 27 | 24 | 26 |

Table 5 shows n-hexanal reduction in a 50:50 mixture of cyclohexyl ketone and cyclohexyl alcohol including 318 parts per million of n-hexanal at time 0. A pH of the mixture was adjusted to 4.5 with addition of formic acid. Table 5 also shows TETA added in five quantities to five identical samples in 1, 2, 3, 4 and 5 molar equivalents to n-hexanal. The samples were stirred at room temperature and gas chromatography measurements of the samples were taken at times 0, 0.1, 0.5, 1, and 12 hours after addition of TETA.

TABLE 6 n-Hexanal Reduction After 60 Minutes
Reflux as a Function of Amine Added

| | pH = 3.1 | | | pH = 4.5 | | |
|---|---|---|---|---|---|---|
| Amine (3 molar equiv.) | Initial ppm | Final ppm | % n-Hexanal Reduct. | Initial ppm | Final ppm | % n-Hexanal Reduct. |
| Hexamethylene Diamine | 320 | 74 | 77 | 360 | 0 | 100 |
| Cyclohexylamine | 283 | 94 | 67 | 254 | 44 | 83 |
| Hexylamine | 296 | 48 | 84 | 312 | 84 | 77 |
| Phenylhydrazine | 292 | 224 | 24 | 307 | 218 | 29 |
| Isobutylamine | 270 | 64 | 69 | 273 | 23 | 92 |
| Octylamine | 276 | 200 | 28 | 273 | 206 | 25 |
| Nonylamine | 208 | 178 | 80 | 209 | 34 | 84 |
| DETA | 250 | 18 | 93 | 260 | 15 | 94 |
| TETA | 344 | 24 | 93 | 375 | 21 | 95 |

Table 6 shows percent n-hexanal reduction in 50:50 mixtures of cyclohexyl ketone and cyclohexyl alcohol including n-hexanal at time 0. A pH of the mixtures was adjusted to 3.1 or 4.5 with addition of formic acid. Table 6 also shows amines added to nine samples in 3 molar equivalents to n-hexanal. Gas chromatography measurements of the samples were taken before and after 60 minutes of reflux of the samples.

TABLE 7 n-Hexanal Reduction After 60 Minutes
Reflux as a Function of Amine Added

| | pH = 5.6 | | | pH = 8 | | |
|---|---|---|---|---|---|---|
| Amine (3 molar equiv.) | Initial ppm | Final ppm | % n-Hexanal Reduct. | Initial ppm | Final ppm | % n-Hexanal Reduct. |
| Hexamethylene Diamine | 305 | 153 | 50 | 280 | 213 | 24 |
| Cyclohexylamine | 207 | 104 | 50 | 191 | 185 | 3 |
| Hexylamine | 322 | 79 | 74 | 300 | 281 | 73 |
| Phenylhydrazine | 342 | 303 | 12 | 324 | 323 | 0 |
| Isobutylamine | 285 | 81 | 76 | 246 | 128 | 48 |
| Octylamine | 306 | 218 | 29 | 312 | 245 | 22 |
| Nonylamine | 207 | 35 | 84 | 210 | 131 | 38 |
| DETA | 255 | 20 | 92 | 251 | 25 | 90 |
| TETA | 301 | 17 | 95 | 270 | 31 | 89 |

Table 7 shows percent n-hexanal reduction in mixtures of 50:50 mixtures of cyclohexyl ketone and cyclohexyl alcohol including n-hexanal. A pH of the mixtures was adjusted to 5.6 or 8 with addition of formic acid. Table 7 also shows amines added to nine samples in 3 molar equivalents to n-hexanal. Gas chromatography measurements of the samples were taken before and after 60 minutes of reflux of the samples.

TABLE 8 n-Hexanal and Cyclohexyl Ketone Reduction
as a Function of Amine Type

| Amine | FW | Boiling Pt (°C.) | % Cyclic Alkanone Reduction | % n-Hexanal Reduction |
|---|---|---|---|---|
| Cyclohexyl Ketone + Cyclohexyl Alcohol | N/A | N/A | <5% | 0 |
| Diphenylamine | 169.23 | 302 | 0 | 0 |
| Melamine | 126.12 | N/A | 0 | 4 |
| Aniline | 93.13 | 184 | 0 | 5 |
| Cyclohexylamine | 99.18 | 134 | <5% | 5 |
| Acetamide | 59.07 | 221 | 0 | 6 |
| Octylamine | 129.25 | 175-177 | <5% | 22 |
| Hexamethylene Diamine | 116.21 | 204 | <5% | 24 |
| Nonylamine | 143.27 | 201 | <5% | 38 |
| Isobutylamine | 73.14 | 64-71 | <5% | 48 |
| Hexylamine | 101.19 | 131-132 | <5% | 73 |
| TETA | 146.24 | 266-267 | 0 | 89 |
| DETA | 103.17 | 199-209 | 0 | 90 |

Table 8 shows percent n-hexanal and cyclohexyl ketone reduction in 50:50 mixtures of cyclohexyl ketone and cyclohexyl alcohol including 300 parts per million n-hexanal. Table 8 shows the amines added to twelve samples in 3 molar equivalents to n-hexanal. The samples were refluxed for thirty minutes. After thirty minutes of reflux of the samples, gas chromatography measurements of the samples were taken.

The invention has been described in an illustrative manner, and it is to be understood that the terminology which has been used is intended to be in the nature of words of description rather than of limitation. Obviously, many modifications and variations of the subject invention are possible in light of the above teachings, and the invention may be practiced otherwise than as specifically described.

What is claimed is:

1. A method of minimizing aldehyde-based impurities in a process stream comprising an alkanone and the aldehyde-based impurities, said method comprising:
   introducing an amine selected from the group of diethylenetriamine, triethylenetetramine, and combinations thereof into the process stream and further comprising adjusting a pH of the process stream to form a heavy product; and separating the alkanone from the heavy product,
   wherein the alkanone comprises cyclohexyl ketone.

2. The method of minimizing aldehyde-based impurities in a process stream as set forth in claim 1 wherein introducing the amine comprises interacting the amine with the aldehyde-based impurities to form the heavy product.

3. The method of minimizing aldehyde-based impurities in a process stream as set forth in claim 2 wherein interacting the amine further comprises chemically reacting the alkanone with the aldehyde-based impurities to form an alkylenyl alkanone as the heavy product.

4. The method of minimizing aldehyde-based impurities in a process stream as set forth in claim 1 wherein the aldehyde-based impurities comprise n-hexanal.

5. The method of minimizing aldehyde-based impurities in a process stream as set forth in claim 1 wherein separating the alkanone from the heavy product comprises distilling the heavy product and the alkanone.

6. The method of minimizing aldehyde-based impurities in a process stream as set forth in claim 5 wherein distilling the heavy product and the alkanone comprises distilling the heavy product and the alkanone at a temperature of from 155° C. to 165° C.

7. The method of minimizing aldehyde-based impurities in a process stream as set forth in claim 1 wherein introducing the amine comprises injecting the amine into the process stream.

8. A method of minimizing aldehyde-based impurities in a process stream as set forth in claim 7 wherein injecting the amine into the process stream comprises injecting the amine into a distillation tower.

9. The method of minimizing aldehyde-based impurities in a process stream as set forth in claim 5 wherein distilling the heavy product and the alkanone comprises distilling the heavy product and the alkanone at a temperature of from 150° C. to 170° C.

10. The method of minimizing aldehyde-based impurities in a process stream as set forth in claim 1 wherein introducing the amine further comprises introducing the amine in an amount of from 0.1 to 10 molar equivalents of the amine compared to the aldehyde based impurities.

11. The method of minimizing aldehyde-based impurities in a process stream as set forth in claim 1 wherein adjusting the pH of the process stream comprises adding an acid to the process stream.

12. The method of minimizing aldehyde-based impurities in a process stream as set forth in claim 1 further comprising heating the process stream to a temperature of from 130° C. to 150° C.

13. A method of minimizing aldehyde-based impurities in a process stream comprising cyclohexyl ketone and n-hexanal, said method comprising:
   introducing an amine into the process stream to form a heavy product and distilling the cyclohexyl ketone from the heavy product.

14. The method of minimizing aldehyde-based impurities in a process stream as set forth in claim 13 wherein introducing the amine comprises interacting the amine with the n-hexanal to form the heavy product.

15. The method of minimizing aldehyde-based impurities in a process stream as set forth in claim 14 wherein interacting the amine further comprises chemically reacting the cyclohexyl ketone with the n-hexanal to form an alkylenyl cyclic hexanone as the heavy product.

16. The method of minimizing aldehyde-based impurities in a process stream as set forth in claim 13 wherein the amine is selected from the group of ethylenediamine, diethylenetriamine, triethylenetetramine, and combinations thereof.

17. The method of minimizing aldehyde-based impurities in a process stream as set forth in claim 13 wherein introducing an amine comprises injecting the amine into a distillation tower.

18. The method of minimizing aldehyde-based impurities in a process stream as set forth in claim 13 wherein distilling the cyclohexyl ketone from the heavy product comprises distilling the heavy product and the cyclohexyl ketone at a temperature of from 150° C. to 170° C.

19. The method of minimizing aldehyde-based impurities in a process stream as set forth in claim 16 wherein distilling the cyclohexyl ketone from the heavy product comprises distilling the heavy product and the cyclohexyl ketone at a temperature of from 155° C. to 165° C.

20. The method of minimizing aldehyde-based impurities in a process stream as set forth in claim 13 wherein introducing the amine further comprises introducing the amine in an amount of from 0.1 to 10 molar equivalents of the amine compared to the n-hexanal.

21. The method of minimizing aldehyde-based impurities in a process stream as set forth in claim 13 further comprising adjusting a pH of the process stream.

22. The method of minimizing aldehyde-based impurities in a process stream as set forth in claim 13 further comprising heating the process stream to a temperature of from 130° C. to 150° C.

23. A method of minimizing aldehyde-based impurities in a process stream used in synthesis of caprolactam, the process stream comprising cyclohexyl ketone and n-hexanal, said method comprising:
   introducing an amine into the process stream to form a heavy product; and distilling the cyclohexyl ketone from the heavy product.

24. The method of minimizing aldehyde-based impurities in a process stream as set forth in claim 23 wherein introducing the amine comprises interacting the amine with the n-hexanal to form the heavy product.

25. The method of minimizing aldehyde-based impurities in a process stream as set forth in claim 24 wherein interacting the amine further comprises chemically reacting the cyclohexyl ketone with the n-hexanal to form an alkylenyl cyclic hexanone as the heavy product.

26. The method of minimizing aldehyde-based impurities in a process stream as set forth in claim 23 wherein the amine is selected from the group of ethylenediamine, diethylenetriamine, triethylenetetramine, and combinations thereof.

27. The method of minimizing aldehyde-based impurities in a process stream as set forth in claim 23 wherein introducing an amine comprises injecting the amine into a distillation tower.

28. The method of minimizing aldehyde-based impurities in a process stream as set forth in claim 23 wherein distilling the cyclohexyl ketone from the heavy product comprises distilling the cyclohexyl ketone and the heavy product at a temperature of from 150° C. to 170° C.

29. The method of minimizing aldehyde-based impurities in a process stream as set forth in claim 26 wherein distilling the cyclohexyl ketone from the heavy product comprises distilling the cyclohexyl ketone and the heavy product at a temperature of from 155° C. to 165° C.

30. The method of minimizing aldehyde-based impurities in a process stream as set forth in claim 23 wherein introducing the amine further comprises introducing the amine in an amount of from 0.1 to 10 molar equivalents of the amine compared to the n-hexanal.

31. The method of minimizing aldehyde-based impurities in a process stream as set forth in claim 23 further comprising adjusting a pH of the process stream.

32. The method of minimizing aldehyde-based impurities in a process stream as set forth in claim 23 further comprising heating the process stream to a temperature of from 150° C. to 170° C.

* * * * *